United States Patent [19]
Burstein et al.

[11] Patent Number: 5,783,557
[45] Date of Patent: Jul. 21, 1998

[54] THF-γ2 ANALOGS AND PHARMACEUTICAL COMPOSITIONS COMPRISING THEM

[75] Inventors: Yigal Burstein; Nathan Trainin, both of Rehovot, Israel

[73] Assignee: Yeda Research and Development Company Ltd at Weizmann Institute of Science, Rehovot, Israel

[21] Appl. No.: 571,985

[22] PCT Filed: Jun. 28, 1994

[86] PCT No.: PCT/US94/07304

§ 371 Date: Mar. 29, 1996

§ 102(e) Date: Mar. 29, 1996

[87] PCT Pub. No.: WO95/01182

PCT Pub. Date: Jan. 12, 1995

[30] Foreign Application Priority Data

Jul. 1, 1993 [IL] Israel ......................... 106214

[51] Int. Cl.$^6$ ................. A61K 38/00; A01N 37/18; C04K 5/00; C04K 7/00
[52] U.S. Cl. ................. 514/11; 514/2; 514/13; 514/14; 514/15; 514/16; 514/17; 514/18; 514/21; 514/885; 530/301; 530/327; 530/328; 530/329; 530/330; 530/331; 530/326; 424/95
[58] Field of Search ................. 424/95; 514/2, 514/11, 14, 13, 16, 17, 18, 15, 21, 885; 530/301, 327, 328, 326, 329, 330, 331

[56] References Cited

PUBLICATIONS

Forino, et al., Side Reactions in the Large-Scale Pharmaceutical Production of THF-gamma2 by Solution Synthesis, Peptides, pp. 257-258, 1992.
Forino, et al., Side-reactions in Peptide Synthesis, Int.J. Peptide Protein Res., vol. 43, pp. 513-519, 1994.
Mizutani, et al., Possible Action of Human Placental Aminopeptidase N in Feto-Placental Unit, Res. Commun. Chem. Pathol. Pharmacol., 82(1), pp. 65-80, Oct. 1993.
Jawetz, Melnick & Adelberg's Medical Microbiology, Nineteen Edition, pp. 367-372, 1991.
Barak et al., "Thymic humoral factor-γ2, an immunoregulatory peptide, enhances human hematopoietic progenitor cell growth" *Exp. Hematol.*, 20:173-177 (1992).
Ben-Hur et al., "Immune modulation exerted by thymic humoral factor THF-γ2 on T cell subsets and IL-2 production . . . " *Immunopharmac and Immunotoxico*, 12(1):(123-133 (1990).
Burstein et al., "Thymic humoral factor γ2: purification and amino acid sequence of an immunoregulatory peptide . . . " *Biochemistry*, 27:4066-4071 (1988).
Goso et al., "Effect of synthetic thymic humoral factor (THF-γ2) on T cell activiies in immunodeficient ageing mice" *Clin. Exp. Immunol.*, 87:346-351 (1992).
Katorza et al., "Restoration of immunological responses by THF, a thymic hormone, in mice infected with murine cytomegalovirus . . . " *Clin. Exp. Immunol.*, 70:268-275 (1987).

Ophir et al., "THF-γ2, a thymic hormone, increases immunocompletence and survival in 5-fluorouracil treated mice . . . " *Cancer immunol and Immunother*, 30:119-125 (1989).
Ophir et al., "A synthetic thymic hormone, THF-γ2, repairs immuno- of mice cured from plasmacytoma by Melphalan" *Int. J. Cancer*, 45:1190-1194, (1990).
Ophir et al., "THF-γ2, a synthetic thymic hormone, increases effectiveness of combined chemotherapy and immunotherapy . . . " *Int. J. Immunopharmac.*, 12:751-754 (1990).
Ophir et al., "Therapeutic effectiveness against MOPC-315 plasmacytoma of low or high does of the synthetic thymic . . . " *Int. J. Cancer*, 48:96-100(1991).
Pecht et al., "The thymic hormone THF-γ2 selectively enhances secretion of IL-2 but not IL-6 by spleen and bone marrow cells" *8th Int'l Congress of Immunology*, Budapest, Abstract (1992).
Pecht et al., "Potentiation of myeloid colony-formation in bone marrow of intact and neonatally thymectomized mice . . . " *Exp. Hematol.*, 21:277-282 (1993).
Rager-Zisman et al., "Therapy of a fatal murine cylomegalovirus infection with thymic humoral factor . . . " *Clin. Exp. Immunol.*, 79:246-252 (1990).
Trainin et al., "Biological and clinical proerties of THF" *Thymus*, 6:137-150 (1985).
Trainin et al., "The use of THF, a thymic hormone . . . " In: *Novel Approaches in Cancer Thereapy*, Lapis & Eckhardt (eds) Karger (Basel)/Akademiai Kiado (Budapest), vol. 5, 253-260 (1987).
The following were cited in the International Search Report of PCT/US94/07304 and were provided with the file as forwarded from the PCT, however, enclosed are copies.
deCastiglione, "Solution synthesis of an octapeptide" EP, A, 0311392 (Apr. 12, 1989).
Indig et al., Hydrolysis of thymic humoral factor γ2 by neutral endopeptidase (EC 3.4.24.11) *Biochem. J.* 278:891-894 (1991).
Handzel et al., "Immunomodulation of T cell deficiency in humans by thymic humoral factor . . . " *J. Biol. Res. Mod.*, 9:269-278 (1990).
Trainin, et al. "Novel THF compositions" U.S.P.N. 4,621, 135, issued Nov. 4, 1986, filed Jun. 6, 1985.

*Primary Examiner*—Robert J. Hill, Jr.
*Assistant Examiner*—Jennifer Harle
*Attorney, Agent, or Firm*—Kohn & Associates

[57] ABSTRACT

The invention relates to analogs of thymic humoral factor γ2 (THF-γ2) having at least 4 amino acid residues and corresponding to the sequence of THF-γ2 of the formula I:

Leu-Glu-Asp-Gly-Pro-Lys-Phe-Leu      I but differing therefrom by addition, deletion or substitution of one or more amino acid residues, or by cyclization, or by linkage of two or more sequences (I) or modified sequences (I) either directly or through a peptidic or non-peptidic chain.

The THF-γ2 analogs of the invention and the functional derivatives and salts thereof are for use as immunomodulatory in pharmaceutical compositions.

5 Claims, No Drawings

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Leu Glu Asp Gly Pro Lys Phe Leu
1               5

( 2 ) INFORMATION FOR SEQ ID NO:2:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Glu Asp Gly Pro Lys Phe Leu
1               5

( 2 ) INFORMATION FOR SEQ ID NO:3:

( i ) SEQUENCE CHARACTERISTICS:

( A ) LENGTH: 6 amino acids
                        ( B ) TYPE: amino acid
                        ( D ) TOPOLOGY: linear ( i i ) MOLECULE TYPE: peptide ( x i ) SEQUENCE DESCRIPTION: SEQ ID NO:3:

Asp  Gly  Pro  Lys  Phe  Leu
        1                   5

( 2 ) INFORMATION FOR SEQ ID NO:4:

( i ) SEQUENCE CHARACTERISTICS:
                        ( A ) LENGTH: 9 amino acids
                        ( B ) TYPE: amino acid
                        ( D ) TOPOLOGY: linear ( i i ) MOLECULE TYPE: peptide ( x i ) SEQUENCE DESCRIPTION: SEQ ID NO:4:

Leu  Glu  Asp  Gly  Pro  Lys  Phe  Leu  Ile
        1                        5

( 2 ) INFORMATION FOR SEQ ID NO:5:

( i ) SEQUENCE CHARACTERISTICS:
                        ( A ) LENGTH: 9 amino acids
                        ( B ) TYPE: amino acid
                        ( D ) TOPOLOGY: linear ( i i ) MOLECULE TYPE: peptide ( x i ) SEQUENCE DESCRIPTION: SEQ ID NO:5:

Tyr  Leu  Glu  Asp  Gly  Pro  Lys  Phe  Leu
        1                        5

( 2 ) INFORMATION FOR SEQ ID NO:6:

( i ) SEQUENCE CHARACTERISTICS:
                        ( A ) LENGTH: 10 amino acids
                        ( B ) TYPE: amino acid
                        ( D ) TOPOLOGY: linear ( i i ) MOLECULE TYPE: peptide ( x i ) SEQUENCE DESCRIPTION: SEQ ID NO:6:

Tyr  Leu  Glu  Asp  Gly  Pro  Lys  Phe  Leu  Ile
        1                        5                        10

( 2 ) INFORMATION FOR SEQ ID NO:7:

( i ) SEQUENCE CHARACTERISTICS:
                        ( A ) LENGTH: 9 amino acids
                        ( B ) TYPE: amino acid
                        ( D ) TOPOLOGY: linear ( i i ) MOLECULE TYPE: peptide ( i x ) FEATURE:
                        ( A ) NAME/KEY: Modified-site
                        ( B ) LOCATION: 1
                        ( D ) OTHER INFORMATION: /note= "The tyrosine residue at
                                position 1 is iodoinated."

( x i ) SEQUENCE DESCRIPTION: SEQ ID NO:7:

Tyr  Leu  Glu  Asp  Gly  Pro  Lys  Phe  Leu
        1                        5

( 2 ) INFORMATION FOR SEQ ID NO:8:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:8:

Tyr Ala Leu Glu Asp Gly Pro Lys Phe Leu
1               5                   10

( 2 ) INFORMATION FOR SEQ ID NO:9:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "X is [D]-alanine"

( x i ) SEQUENCE DESCRIPTION: SEQ ID NO:9:

Xaa Leu Glu Asp Gly Pro Lys Phe Leu
1               5

( 2 ) INFORMATION FOR SEQ ID NO:10:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:10:

Leu Glu Asp Gly Pro Lys Phe Leu Ala Tyr Ala Leu Glu Asp Gly Pro
1               5                   10                  15

Lys Phe Leu ( 2 ) INFORMATION FOR SEQ ID NO:11:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:11:

Leu Ser Asp Gly Pro Lys Phe Leu
1               5

( 2 ) INFORMATION FOR SEQ ID NO:12:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:12:

Leu Phe Asp Gly Pro Lys Phe Leu
1               5

-continued ( 2 ) INFORMATION FOR SEQ ID NO:13:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Leu Glu Ala Gly Pro Lys Phe Leu
1               5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

Leu Glu Arg Gly Pro Lys Phe Leu
1               5

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Leu Glu Asp Asp Pro Lys Phe Leu
1               5

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Leu Glu Asp Val Pro Lys Phe Leu
1               5

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Leu Glu Asp Tyr Pro Lys Phe Leu
1               5

( 2 ) INFORMATION FOR SEQ ID NO:18:

( i ) SEQUENCE CHARACTERISTICS:
        ( A ) LENGTH: 8 amino acids
        ( B ) TYPE: amino acid (D) TOPOLOGY: linear (ii) MOLECULE TYPE: peptide (xi) SEQUENCE DESCRIPTION: SEQ ID NO:18:

Leu Glu Asp Gly Ser Lys Phe Leu
    1               5

(2) INFORMATION FOR SEQ ID NO:19:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:19:

Leu Glu Asp Gly Arg Lys Phe Leu
    1               5

(2) INFORMATION FOR SEQ ID NO:20:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:20:

Leu Glu Asp Gly Gln Lys Phe Leu
    1               5

(2) INFORMATION FOR SEQ ID NO:21:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:21:

Leu Glu Asp Gly Pro Lys Val Leu
    1               5

(2) INFORMATION FOR SEQ ID NO:22:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:22:

Leu Glu Asp Gly Pro Lys His Leu
    1               5

(2) INFORMATION FOR SEQ ID NO:23:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:23:

```
        Leu Glu Asp Gly Pro Lys Ala Leu
        1               5
```

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
        Leu Glu Asp Gly Pro Lys Ser Leu
        1               5
```

( 2 ) INFORMATION FOR SEQ ID NO:25:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
        Met Glu Asp Ser Pro Lys Phe Val
        1               5
```

( 2 ) INFORMATION FOR SEQ ID NO:26:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
        Leu Glu Asn Gly Gln Lys Phe Asp
        1               5
```

( 2 ) INFORMATION FOR SEQ ID NO:27:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
        Leu Glu Cys Gly Pro Cys Phe Leu
        1               5
```

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

```
        Leu Cys Ala Gly Pro Cys Phe Leu
        1               5
```

THF-γ2 ANALOGS AND PHARMACEUTICAL
COMPOSITIONS COMPRISING THEM

FIELD OF THE INVENTION

The present invention relates to synthetic immunoregulatory peptides which are analogs of thymic humoral factor THF-γ2 (hereinafter THF-γ2) and to pharmaceutical compositions comprising them.

BACKGROUND OF THE INVENTION

THF-γ2, an immunologically active peptide of the sequence Leu-Glu-Asp-Gly-Pro-Lys-Phe-Leu(SEQ ID No:1), has been isolated and purified from calf thymus homogenates and also prepared synthetically (U.S. Pat. No. 4,621,135; Burstein et al., 1988).

THF-γ2 has been shown to possess many biological activities. For example, it was found to augment T cell functions, such as the proliferative response to the T cell mitogens phytohemagglutinin (PHA) and concanavalin A (ConA), the mixed lymphocyte reaction (MLR) and the ConA induced IL-2 production. Increased IL-2 production was shown by spleen cell cultures treated with THF-γ2 prior to their triggering with ConA. THF-γ2 was effective in augmenting IL-2 activity in low IL-2 producer mouse strain C3B6F1 spleen cell cultures by 100–150%, relative to control untreated cultures, at an optimal concentration of 100–300 ng/ml (Burstein et al., 1988).

THF-γ2 modulates the immune state and response of human umbilical cord blood lymphocytes (UCBL). Thus, preincubation of UCBL with THF-γ2 increased the percentage of cells expressing the CD4 or the CD8 differentiation antigens. THF-γ2 increased likewise PHA-induced IL-2 secretion of UCBL cultures by treatment prior to suboptimal PHA stimulation. This effect was THF-γ2 dose dependent with an optimum in the range of 300–600 ng/ml and was not influenced by irradiation of the UCBL (Ben-Hur et al., 1990).

THF-γ2 was shown to have an effect on the immune competence of neonatally thymectomized (NTx) mice, which show a depressed immune response compared to intact age-matched mice. A biweekly course of THF-γ2 injections caused a partial to complete restoration of the immune functions as determined ex-vivo by PHA, ConA, MLR and IL-2 activity. In dose escalation studies, using THF-γ2 at doses of 4, 40 and 400 ng/Kg, the optimal daily dose was found to be 4 ng/Kg (Handzel et al., 1990). Neonatal thymectomy (NTx) of BALB/c mice caused a decrease in myeloid progenitors, which was repaired by serial injections of THF-γ2. The repair of the stem cell compartment in the bone marrow correlated with an increased percentage of Thy1[30] cells in the spleen of THF-γ2 treated NTx mice, indicating that THF-γ2 is able to regulate committed stem cell functions in the bone marrow of immune deprived NTx mice (Pecht et al., 1993).

THF-γ2 was also shown to cause restoration of immune response in mice infected with murine cytomegalovirus (MCMV), which represents a model for the study of the role of the immune system in the pathogenesis of human CMV. Cytomegalovirus causes T cell immune impairment in infected mice, reflected by a decreased response to the T cell mitogens PHA and ConA, reduction of ConA-induced IL-2 secretion, a marked increase in the spleen weight and development of liver focal hepatitis. Systemic treatment of MCMV-infected mice with THF-γ2 resulted in a reconstitution of the mitogenic responses, IL-2 secretion, normalization of spleen weight and recovery of liver inflammation.

Unlike other thymic hormones, THF-.γ2 did not affect interferon synthesis and NK (Natural Killer) cytotoxicity in MCMV-infected mice, suggesting that THF-γ2 restores immune competence of these immunosuppressed mice through modulation of the T cell compartment (Katorza et al., 1987). Adoptive transfer experiments were performed to evaluate the prospects of enhancing the antiviral potential of MCMV immune spleen cells by THF-γ2. MCMV-resistant adult BALB/c mice become highly susceptible following immunosuppression by cyclophos-phamide (CY). Recipient mice were injected with MCMV and CY concomitantly and 24 hours later, adoptive transfers of syngeneic MCMV-immune spleen cells were performed. It was shown that passive transfers of MCMV immune spleen cells prevented the development of a fatal disease in 38% of the recipient mice. Daily injections of MCMV immune donor mice with THF-γ2 considerably enhanced (93%) the therapeutic potential of virus specific immune cells. These results provide direct evidence for the antiviral activity of THF-γ2 through its immunomodulatory effect on immune T cells. (Rager-Zisman et al., 1990)

THF-γ2 did not affect IFN-y production either in vitro with cultured cells (Trainin et al., 1985) or in vivo in MCMV-infected mice (Katorza et al., 1987).

THF-γ2 also has an adjuvant effect on chemotherapy in mouse plasmacytomas MOPC-315 and RPC-5. Under certain conditions, chemotherapy with antineoplastic alkylating drugs, such as cyclophosphamide or Melphalan (L-PAM), may facilitate the development of an antitumor immune response against MOPC-315 plasmacytoma. This immune promoting effect of the drug is expressed, in vivo, by cure and induction of resistance to challenge, and in vitro, by increase in specific cytotoxic potential of spleen cells from treated tumor-bearing mice. Another antineoplastic drug, 5-fluorouracil (5-FU), is capable of inducing a regression of MOPC-315 tumors, but does not lead to the development of a host antitumor response. Therefore, the influence of THF-γ2 in both situations was tested, either with L-PAM or with 5-FU (Trainin et al., 1987). The effect of THF-γ2 on the immune competence of 5-FU treated MOPC-315 tumor-bearing BALB/c mice was examined. Treatment of noninoculated or tumor-bearing mice with THF-γ2 after 5-FU injection, resulted in an increase in the antibody response to sheep red blood cells (SRBC) and of the allogeneic response in spleen cell cultures, but had no effect on the ConA-induced IL-2 secretion over that caused by 5-FU alone. Treatment with either 5-FU alone or 5-FU and THF-γ2 resulted in restoration to normal values of Lyt-1 (CD3) and L3T4 (CD4) positive populations in tumor-bearing mice. THF-γ2 prolonged the survival time of MOPC-315 tumor bearing mice over that observed in mice treated with 5-FU alone (Ophir et al., 1989), and a mega dose (50 μg/injection) was more effective than the low dose (0.4 ng/injection) (Ophir et al., 1991).

BALB/c mice cured from large MOPC-315 tumors by Melphalan, remain deficient in their spleen T cell function. Administration of THF-γ2 to cured mice repaired their immunodeficiency as evidenced in in vitro tests with spleen cells by increase of ConA induced IL-2 secretion, allogeneic response in MLR, generation of primary antibody response and restoration of relative percentages of T cell subsets to normal values (Ophir et al., 1990).

RPC-5 murine plasmacytoma, induced by intraperitoneal injection of mineral oil, is resistant to chemotherapy with alkylating drugs. This tumor is able to induce a specific host antitumor immune response as shown by the finding that spleen cells from RPC-5 immunized mice were effective for adoptive immunotherapy (AIT) in combination with Melphalan. Treatment of RPC-5 immunized mice with THF-γ2 increased the specific cytotoxic response in vitro of their spleen cells and also improved the effectiveness of these cells in AIT of RPC-5 tumor-bearing mice when performed in combination with chemotherapy by Melphalan (Ophir et al., 1990).

THF-γ2 was also shown to have an effect on human granulocyte macrophage colony-forming cells (GM-CFC) and erythroid burst-forming units (BFU-E). Bone marrow (BM), peripheral blood (PB) or cord blood (CB) mononuclear cells of normal human donors were incubated overnight with various concentrations of THF-γ2, washed and assayed in the GM-CFC or BFU-E agar culture assay systems stimulated by granulocyte macrophage colony-stimulation factor (GM-CSF) or erythropoietin, respectively. In several experiments lymphoid cells were removed by treatment with an anti T cell antibody, CAMPATH-1, and complement. THF-γ2 significantly enhanced, in a dose-related pattern, the in vitro growth of normal human BM-GM-CFCs. This effect was GM-CSF dependent with maximal enhancement of 156% of the number of colonies relative to control cultures obtained with 25 ng/ml of THF-γ2. T cell depletion by CAMPATH-1 with complement did not abrogate the THF-γ2 induced enhancement of BM-GM-CFC growth. THF-γ2 also exerted a significant dose response enhancement of normal PB-BFU-E growth and CB-BFU-E, an indirect effect totally abrogated by treatment with CAMPATH-1 and complement (Barak et al., 1992).

THF-γ2 has a potentiating effect in vitro on myeloid progenitor cells in murine bone marrow, as determined on committed stem cells of bone marrow origin using the myeloid progenitor cell clonal assay. Preincubation of normal BM cells with THF-γ2 for 1 h caused a 2–5 fold increase in the number of myeloid colonies in the presence of suboptimal concentrations of CSF but it did not replace CSF as an inducer. The optimal dose of THF-γ2 causing this enhancement was in the range of 25–100 ng/ml. The super-additive effect of THF-γ2 was not mediated via IL-6, since it did not induce IL-6 activity upon 24 h incubation with BM cells nor enhanced LPS-induced IL-6 secretion by bone marrow cells in vitro (Pecht et al., 1993).

THF-γ2 was shown to have an effect on functions of the central nervous system. Electrophysiological experiments have demonstrated changes in the electrical activity of single neurons within the endocrine hypothalamus during an immune response. These changes can be recorded in conscious rats while the immune response is taking place. Experiments were carried out using conscious male rats bearing chronic electrodes for EEG recording and preoptic area (POA) multi-unit activity (MUA). In order to examine possible effects upon EEG and POA MUA, animals were also implanted with intracerebroventricular cannulae for administration of immune system factors. Saline (50 μl) administration slightly increased POA MUA up to 45 min following injection and also increased the total time and duration of synchronized (sleep) EEG periods, while THF-γ2 (0.2 ng/50 μl) significantly reduced POA MUA and increased the amount and duration of synchronized EEG. These results indicate that THF-γ2 is able to alter state of arousal as well as the neural activity in an area of the brain known to be of importance in the modulation of both immune and neuroendocrine activity, and that it might be useful for these purposes in clinical practice (Saphier et al., 1988).

THF-γ2 was shown to be an effective immune-modulator in restoring immunodeficient aging mice. A single low dose injection of THF-γ2 (16 ng/mouse) was found to enhance the frequency of ConA-responsive cells in thymus and spleen cell populations, as well as the frequency of cytokine-producing splenic T cells, up to the levels observed in young mice. The capacity of mitogen-stimulated spleen cells to produce T cell growth factor (TCGF) was also elevated. The treatment of aging mice with THF-γ2 also resulted in an increased helper activity of the spleen cells to antibody producing cells (Goso et al., 1992). These results corroborate our previously reported findings on the enhancement of THF-γ2 induced mitogen driven IL-2 production in mice (Katorza et al., 1987; Burstein et al., 1988) and humans (Ben-Hur et al., 1990), and restoration of helper activity to the anti-SRBC response in tumor plus chemotherapy-induced immunodeficiency (Ophir et al., 1989).

Preliminary clinical trials have been performed with synthetic THF-γ2 in an open, nonrandomized pilot clinical study conducted on a group of patients with various lymphoproliferative disorders (four lymphomas, three acute lymphatic leukemias, one histiocytosis-X), one neuroblastoma, and one rhabdomyosarcoma. All were subjected to repeated pulses of combined chemotherapy and maintenance treatment, resulting in a reduction of circulating T cells and their functions. The patients were free of infection at the time of enrolment in the trial. Dosages for patients were extrapolated from the experiments on NTx mice, the lowest dosage was chosen for the clinical trials. The efficacy of treatment was evaluated by various clinical criteria, including specific signs of infection, fever rashes, general feeling of well-being, etc., and multiple laboratory parameters were monitored. Peripheral blood lymphocytes and total circulating T cells were counted. Monoclonal antibodies were used to detect T cells CD2, CD3 and their sub-populations CD4 and CD8, as well as NK cells; proliferative responses of T cells to the mitogens PHA and Con-A were compared to those of normal controls. During treatment with synthetic THF-γ2, all patients, except one, were in complete clinical remission from their basic disease. No clinical benefit was expected, since patients free from complications were explicitly selected, according to the protocol of the Israel Health Ministry. Synthetic THF-γ2 treatment consisted of a 3-week course of daily i.m. injections, at a dosage of 4 ng/kg/day, 6 days/wk, for a total of 18 injections. All patients were monitored for potential adverse side effects. Following treatment, T cell populations were markedly enhanced in 70% of the patients, with a trend toward normalization of CD4/CD8 ratios, and mitogenic responses were also improved. In addition, negative delayed type hypersensitivity reaction tests became positive in four of the five patients who were tested. The results demonstrated that the pattern of immune reconstitution induced by synthetic THF-γ2 was similar to that obtained with the different fractions of biological THF and THF-γ2. Furthermore, a marked increase of NK cell population was perceived. No side effects attributable to synthetic THF-γ2 were observed during this trial.

Following the above pilot study, synthetic THF-γ2 was introduced in Israel for treatment of disseminated infections, especially of viral origin. Four patients suffering from severe viral infections of the herpes group, associated with various immune impairments, were treated with synthetic THF-γ2, following the same protocol described previously. A rapid regression of the viral infections was observed, similar to that seen with biological THF. A remarkable enlargement of T cell populations was observed in all cases and, as before, no deleterious side effects were documented. The results confirmed that the efficacy of synthetic THF-γ2 as an immunomodulator of T cell impairments, with a marked therapeutic effect against viral infections, is identical to that seen with biological THF in prior studies (Handzel, et al., 1990).

DESCRIPTION OF THE INVENTION

It has now been found in accordance with the present invention that certain synthetic peptides that are analogs of THF-γ2 have immuno-modulatory properties similar to THF-γ2. These peptides substantially enhance ConA-induced IL-2 production in mouse spleen cells and/or the number of colonies of GM-CFC of mouse bone marrow in the presence of growth factors GM-CSF and IL-3.

The peptides according to the invention have at least four amino acid residues and comprise one or more sequences corresponding to the THF-γ2 sequence of the formula I:

Leu-Glu-Asp-Gly-Pro-Lys-Phe-Leu(SEQ ID NO:1)    (I)

but differing therefrom by
(i) deletion of from one to four amino acid residues;
(ii) addition of one or more amino acid residues at the N- and/or C-terminus;
(iii) substitution of one or more amino acid residues by a protein natural or non-natural amino acid residue;
(iv) cyclization through a free carboxyl group and a free amino group or through disulfide bonds of cysteine residues; or
(v) linkage of two or more sequences of sequence (I) or modified sequences of (I) corresponding to anyone of (i), (ii), (iii) or (iv) above, either directly or through a peptidic or non-peptidic chain.

By "substantially enhancing the ConA-induced IL-2 production in mouse spleen cells" it is intended to mean according to the invention that the production of IL-2 is increased by at least 30%, relative to the control, at two consecutive two-fold dilutions, in the range of 18–300 ng/ml. By "substantially enhancing the number of GM-CFC of mouse bone marrow in the presence of growth factors GM-CSF and IL-3" it is intended to mean according to the invention that the the number of GM-CFC is increased by at least 30%, relative to the control, at two consecutive two-fold dilutions, in the range of 25–200 ng/ml.

From all the peptides tested, those obtained by addition of one or more, particularly of one or two amino acid residues were the most active. Examples are addition of amino acid residues, like Tyr at the N-terminus before the Leu$^1$ residue ($Y^{31}$ $^1$-THF-γ2 in Table 3) or Ile at the C-terminus after the Leu$^8$ residue ($I^9$ -THF-γ2 in Table 3) or addition at both N- and C-terminus groups ($Y^{-1}$, $I^9$-THF-γ2).

According to the invention, deletion of only one or two amino acid residues are preferred when deletion is made, thus leading to peptides of at least six amino acid residues. Thus, active peptides were obtained by deletion of the Leu residue at position 1 (Des L$^1$-THF-γ2) or both Leu$^1$ and Glu$^2$ (Des L$^1$, E$^2$-THF-γ2) of THI-γ2.

Substitution of one or more, preferably one, amino acid residues of the sequence (I) by different amino acid residues are a further embodiment of the invention. Thus, active peptides were obtained by single substitution of Leu by Arg at position 1; Glu by Ser, Gln or Phe at position 2; of Asp by Ala, Arg or Phe at position 3; of Gly by Tyr, Val, Asp or Ser at position 4; of Pro by Ala, Lys, Gln, Ser or Arg at position 5; of Lys by Asp, Tyr, Asn or Ile at position 6; of Phe by Val, His, Ala, Ser, Tyr, Asn or Glu at position 7; and of Leu by Gln, His or Lys at position 8 of the THF-γ2 molecule. Active peptides were also obtained by substitution of two, three and four amino acid residues, as shown in Table 3.

The amino acid residues added to or used for substitution in the THF-γ2 molecule may be derived from natural protein amino acids in the L form and/or from the non-natural form, such as the D (retro) form or modified residues such as the ornithine, β-alanine, citrulline and the like.

Also encompassed by the present invention are compounds comprising two or more THF-γ2 molecules or modified THF-γ2 molecules as defined above, linked directly through the N-terminus of one molecule and the C-terminus of the other molecule, or linked through an amino acid residue or a peptidic chain of at least two amino acids or through a non-peptidic chain. The non-peptidic chain may be aliphatic or aromatic and is derived from a bifunctional compound comprising terminal amino and/or carboxyl groups at both ends. Preferred are peptides comprising two sequences of THF-γ2 linked by a peptidic chain of from 2 to 5, preferably 3, amino acid residues. Particularly active was a peptide of nineteen amino acid residues comprising two molecules of THF-γ2 linked by an Ala-Tyr-Ala [(THF-γ2)-A-Y-A-(THF-γ2) in Table 3] tripeptide(SEQ ID No:10).

Further encompassed by the present invention are cyclic peptides, such as peptides obtained by cyclization through the free β-carboxyl group of an Asp residue or the free γ-carboxyl group of a Glu residue with the free ε-amino group of a Lys residue, as well as through cyclization of the α-amino group of the peptide with its (α-carboxyl group, or through disulfide bonds between cysteine residues.

As used herein, the term "functional derivatives" refers to derivatives of free —OH, —SH, —NH$_2$ and —COOH groups, such as substitution of hydroxy groups of Tyr by halogen, e.g. iodo, and to ethers, esters, amides, and similar derivatives presenting chemical moieties not normally a part of the peptide. Examples of such substitutions are aminocaproyl, acetyl, and biotinyl. The term "salts" of the peptides and of the functional derivatives thereof comprises salts of free carboxyl groups with organic or inorganic bases and acid addition salts of free amino groups. All analogs of THF-γ2, functional derivatives and salts thereof are encompassed by the invention as long as they are biologically active, being capable of enhancing IL-2 production induced by ConA in mouse spleen cells and/or GM-CFC number from mouse bone marrow.

The peptides of the invention are for use as immuno-modulatory and thus may be used in the preparation of immunomodulatory pharmaceutical compositions.

The invention further comprises pharmaceutical compositions comprising as active ingredient a peptide of the invention, a functional derivative or salt thereof, and a pharmaceutically acceptable carrier. These pharmaceutical compositions are suitable for the treatment of several disorders, including: congenital immune defects involving primary T cell deficiencies, such as thymic displasia and Down's syndrome; primary and secondary viral infections (e.g. herpes virus, adenovirus), and HIV, as well as subacute infections, such as subacute sclerosing panencephalitis (SSPE) alone or in combination with antiviral drugs; immune suppression and leukopenia following cancer treatment by chemotherapy and/or radiotherapy; autoimmune inflammatory disorders, e.g. rheumatoid arthritis, systemic lupus erythematosus and psoriasis; in bone marrow transplantation with the aim of preventing cytomegalovirus and other viral infections; in a topic conditions, such as asthma, a topic dermatitis and the like.

The pharmaceutical compositions of the invention will be used in a similar way as compositions containing biologic or synthetic THF-γ2. For instance, solutions for parenteral or intranasal administration may be obtained by extemporaneous reconstitution of freeze-dried formulation of the active peptide analog with sterile water or sterile aqueous isotonic solution, such as sodium chloride for injection. The solvent for reconstitution may also contain a suitable, pharmaceutically acceptable preserving agent. Considering that the amount of drug substance may not give an adequate solid cake as residue, a bulking agent may be included in the lyophilized formulation, to obtain a compact freeze-dried cake with good mechanical strength. Suitable bulking agents include lactose, mannitol, dextrose, etc. A pH-adjusting agent may also be present in the formulation.

The invention will now be illustrated by the following non-limiting examples.

EXAMPLES

Example 1—Bioassays of THF-γ2

Bioassays for THF-γ2 enabling a more specific and sensitive monitoring were developed based on our understanding of the mechanisms of regulation of T cell differentiation and maturation and the involvement of cytokines. Thus, in a first bioassay, the effect on mitogen-induced IL-2 production, a T-helper cell activity reflecting post-thymus maturation is assessed. Since THF-γ2 has also a pre-thymic function in up-regulating myeloid committed stem cells, we employed this as a sensitive bioassay to complement the first.

1.1. ConA-Induced IL-2 Production

In this bioassay, the effect of THF-γ2 and its analogs in enhancing the secretion of ConA-induced IL-2 from murine spleen cells is determined.

1.1.1. Preparation of cells and preincubation with THF-γ2. Pooled spleen cells ($10^7$ cell/ml) from five female C3B6F1 (C3HeB/FeJ×C57BL/6J) mice (obtained from Jackson Labs, U.S.A.) aged 6–8 weeks are seeded in 24-well plates (Costar, Cambridge, Mass. U.S.A.). The cells are prepared in medium RPMI-1640 supplemented with penicillin (100 u/ml), streptomycin (100 µg/ml), 2 mM glutamine, 50 µM 2-mercaptoethanol (2-ME) and 20 mM HEPES. THF-γ2 in various concentrations in phosphate buffered saline (PBS), is added in 20 µl aliquots, while control cultures receive 20 µl PBS. The cell cultures are incubated for 20 h in a humidified incubator of 5% $CO_2$/95% air and 37° C.

1.1.2. Induction of IL-2. ConA (Concanavalin A, ConA, 3×crystalline, Bio-Makor, Ness-Ziona, Israel) is added to the wells in 1 ml fresh medium (as in 1.1.1 above) at suboptimal concentration (1–2.5 µ/ml). After 3 h the plates are centrifuged at 1200 rpm (Sorvall GLC-3 centrifuge), the supernatant is removed and replaced by 1 ml of fresh medium (as in 1.1.1 above) and the cultures are further incubated for 20 h. The plates are then centrifuged, the supernatants are collected and kept at −20° C.

1.1.3. Assay on CTL-D, an IL-2 dependent T cell line. Supernatants from 1.1.2 above (50 µl) are added at serial two fold dilutions (1:2–1:64), in triplicate, to U-bottomed microwells (Greiner, Germany) containing $1\times10^4$ CTL-D cells in 50 µl RPMI-1640 (as in 1.1.1 above) supplemented with 1 mM sodium pyruvate, 1 mM non-essential amino acids and 10% FCS (Beth-Haemek, Israel). After incubation of 48 h at 37° C./5% $CO_2$, the proliferation is assessed by the MTT colorimetric assay (T. Mosmann, J. Immunol. Methods 65: 55–63, 1983). Results are expressed in units/ml calculated using a standard murine IL-2 preparation (according to S. Gillis et al., J. Immunol. 120: 2027, 1978).

1.2. Effect of THF-γ2 on GM-CFC From Mouse Bone Marrow.

In this second bioassay, the effect of THF-γ2 and its analogs in the enhancement of the number of colonies of GM-CFC in the presence of growth factors is determined.

1.2.1. Preparation of bone marrow cells. Tibia and femur were removed from BALB/c female mice (6–8 weeks old). The tip of the bone was cut and DMEM with 2.5% FCS was flushed into the bone using a 1 ml syringe with a 26 G needle. This procedure was repeated twice, the cells were then washed in medium and counted in the presence of trypan blue.

1.2.2 Preincubation with THF-γ2. Bone marrow cells suspension was prepared in DMEM with 2.5% FCS at a concentration of $15\times10^6$/3.0 ml. THFγ2 diluted in DMEM was added in 20 µl aliquots, control cells received 20 µl DMEM. Cell suspensions in conical tissue culture tubes were incubated at 37° C./8% $CO_2$ for 1 h. Cells were then collected, washed and counted in trypan blue. Cell suspensions were adjusted at $1\times10^6$/ml.

1.2.3. GM-CFC assay. Bone marrow cells ($4\times10^5$) are suspended in methylcellulose (0.8%), FCS (20%) and conditioned medium of 14FIL3 CB6 cell line (5%) in a total volume of 4 ml of DMEM. After vigorous mixing, the suspension is seeded into 30 mm diameter plates with the aid of a 3.0 ml syringe (21G needle, in triplicate). The small plates are placed in a large plate (20 cm) alongside one open, small plate containing water, in order to maintain high humidity, and incubated at 37° C. in an 8% $CO_2$ incubator for 7 days. Colonies are counted using an inverted microscope at low magnification.

Example 2. Chemical Synthesis and Biological Activity of the THF-γ2 Analogs

To design potent THF-γ2 analogs for possible use as immunologicaly active drugs, peptide analogs of THF-γ2 were synthesized and their biological activity studied.

The peptides were synthesized by the Merrifield technique [Merrifield R. B., J. Am. Chem. Soc. (1963) 85: 2149], using PAM resins (Applied Biosystems, Inc. Foster City, Calif). According to this procedure, activated protected amino acid residues were coupled sequentially to the insoluble polymers. After completion of coupling of the last amino acid, when required, the side chain protecting groups of the residues to be biotinylated or involved in cyclic peptide or depsipeptide bond formation, were deblocked and the resulting side chain functionalities were derivatized with a biotinylating agent or made to react via the suitable cyclization reagent. The peptides were then fully deblocked and removed from the resin using anhydrous HF, treated with ether and extracted with aqueous acetic acid. The crude mixture was then purified by filtration on Bio-gel P-2 or Sephadex G-10 gels. When needed, the semi-purified peptide was exposed to a suitable oxidative agent in dilute solutions, in order to obtain the corresponding intramolecular disulfide derivative. Further purification was achieved by reversed phase high-performance liquid chromatography (RP-HPLC) on C-18 columns, using gradients of acetonitrile at acidic pH (such as a mixture of $NaClO_4$ and $H_3PO_4$ or $CF_3COOH$). The final purification steps employed trifluoroacetic acid, yielding trifluoroacetate salts of the isolated peptides. The isolated and purified peptide analogs of THF-γ2 were characterized by amino acid composition analysis on a Dionex BioLC automatic amino acid analyzer, and their amino acid sequence determined using ABI Model 475 protein microsequencer. Analyses were performed according to the specifications of the manufacturers.

Several series of peptide analogs of THF-γ2 were synthesized. These included addition, deletion and substitution of amino acid residues of THF-γ2, as well as analogs obtained by biotinylation of native or added lysine residues, or through side-chain to side-chain cyclization. Over 100 peptides were synthesized (Tables 1 and 2) and their biological activity was assayed, as described in Example 1. The results for 48 of these peptides are shown in Table 3 (+++: strong enhancement, as THF-γ2; ++ and +: medium and weak enhancement, lower than THF-γ2:—no activity; n.d.: not done).

In the tables, THF-γ2 stands for the sequence I. Additions at the N-terminus are indicated by the single letter amino acid code with an upper negative number, e.g. $Y^{-1}$ and $Y^{-2}$, $A^{-1}$, and at the C-terminus by a positive number higher than 8, e.g. $I^9$; deletion is indicated by des- together with the deleted residue, e.g. des-$L^1$, des-$L^1$,$E_2$; substitution is indicated by the single letter code of the amino acid replacing the original residue and the position of the substitution, e.g. $A^3$-THF-γ2 indicates that Asp at position 3 is replaced by Ala.

The following are examples of full-sequences of peptides according to the invention that appear in concise form in the tables: des-$L^1$-THF-γ2 Glu-Asp-Gly-Pro-Lys-Phe-Leu (SEQ ID No:2) des-$L^1$, $E^2$-THF-γ2 Asp-Gly-Pro-Lys-Phe-Leu (SEQ ID No:3) $I^9$-THF-γ2 Leu-Glu-Asp-Gly-Pro-Lys-Phe-Leu-Ile (SEQ ID No:4) $Y^{-1}$-THF-γ2 Tyr-Leu-Glu-Asp-Gly-Pro-Lys-Phe-Leu (SEQ ID No:5) $Y^{-1}$, $I^9$-THF-γ2 Tyr-Leu-Glu-Asp-Gly-Pro-Lys-Phe-Leu-Ile (SEQ ID No:6) Iodo-$Y^{-1}$-THF-γ2 Iodo-Tyr-Leu-Glu-Asp-Gly-Pro-Lys-Phe-Leu (SEQ ID No:7) $Y^{-2}$, $A^{-1}$-THF-γ2 Tyr-Ala-Leu-Glu-Asp-Gly-Pro-Lys-Phe-Leu (SEQ ID No:8) [D] $A^{-1}$-THF-γ2 [D]-Ala-Leu-Glu-Asp-Gly-Pro-Lys-Phe-Leu (SEQ ID No:9) (THF-γ2)-A-Y-A-(THF-γ2) Leu-Glu-Asp-Gly-Pro-Lys-Phe-Leu-Ala-Tyr-Ala-Leu-Glu-Asp-Gly-Pro-Lys-Phe-Leu (SEQ ID No:10) $S^2$-THF-γ2 Leu-Ser-Asp-Gly-Pro-Lys-Phe-Leu (SEQ ID No:11) $F^2$-THF-γ2 Leu-Phe-Asp-Gly-Pro-Lys-Phe-Leu (SEQ ID No:12) $A^3$-THF-γ2 Leu-Glu-Ala-Gly-Pro-Lys-Phe-Leu (SEQ ID No:13) $R^3$-THF-γ2 Leu-Glu-Arg-Gly-Pro-Lys-Phe-Leu (SEQ ID No:14) $D^4$-THF-γ2 Leu-Glu-Asp-Asp-Pro-Lys-Phe-Leu (SEQ ID No:15) $V^4$-THF-γ2 Leu-Glu-Asp-Val-Pro-Lys-Phe-Leu (SEQ ID No:16) $Y^4$-THF-γ2 Leu-Glu-Asp-Tyr-Pro-Lys-Phe-Leu (SEQ ID No:17) $S^5$-THF-γ2 Leu-Glu-Asp-Gly-Ser-Lys-Phe-Leu (SEQ ID No:18) $R^5$-THF-γ2 Leu-Glu-Asp-Gly-Arg-Lys-Phe-Leu (SEQ ID No:19) $Q^5$-THF-γ2 Leu-Glu-Asp-Gly-Gln-Lys-Phe-Leu (SEQ ID No:20) $V^7$-THF-γ2 Leu-Glu-Asp-Gly-Pro-Lys-Val-Leu (SEQ ID No:21) $H^7$-THF-γ2 Leu-Glu-Asp-Gly-Pro-Lys-His-Leu (SEQ ID No:22) $A^7$-THF-γ2 Leu-Glu-Asp-Gly-Pro-Lys-Ala-Leu (SEQ ID No:23) $S^7$-THF-γ2 Leu-Glu-Asp-Gly-Pro-Lys-Ser-Leu (SEQ ID No:24) $M^1$, $S^4$, $V^8$-THF-γ2 Met-Glu-Asp-Ser-Pro-Lys-Phe-Val (SEQ ID No:25) $N^3$, $Q^5$, $D^8$-THF-γ2 Leu-Glu-Asn-Gly-Gln-Lys-Phe-Asp (SEQ ID No:26)

TABLE 1

Peptide Analogs of THF-γ2

| Peptide | Relative retention time<sup>a</sup> $R_t$ (peptide)/$R_t$ (THF-γ2)<sup>b</sup> |
|---|---|
| THF-γ, L-E-D-G-P-K-F-L<sup>c</sup> (SEQ ID NO: 1) | 1.00 |
| Extension/Addition analogs | |
| (THF-γ2)-A-Y-A-(THF-γ2) | 2.54 |
| $Y^{-1}$-THF-γ2 | 1.28 |
| iodo-$Y^{-1}$-THF-γ2 | 1.58 |
| diiodo-$Y^{-1}$-THF-γ2 | 1.92 |

TABLE 1-continued

Peptide Analogs of THF-γ2

| Peptide | Relative retention time<sup>a</sup> $R_t$ (peptide)/$R_t$ (THF-γ2)<sup>b</sup> |
|---|---|
| $I^9$-THF-γ2 | 1.40 |
| $Y^{-1}$,$I^9$-THF-γ2 | 1.62 |
| $K^{-1}$-THF-γ2 | 0.99 |
| $K^{-1(\epsilon\text{-AC-biotinyl})}$-THF-γ2‡ | 1.41 |
| [D]$A^{-1}$-THF-γ2 | 1.24 |
| N-Acetyl-THF-γ2 | 1.56 |
| ε-AC-THF-γ2‡ | 1.24 |
| THF-γ2-NH$_2$ | 0.87* |
| $K^{-1}$,$K^{-2}$,$G^{-3}$,$K^9$,$S^{10}$,$G^{11}$-THF-γ2 | 0.71* |
| $K^{6(\epsilon\text{-AC-biotinyl})}$-THF-γ2‡ | 1.53 |
| $K^{6(\epsilon\text{-L-E-D-G})}$-THF-γ2 | 1.13 |
| $A^{-1}$-THF-γ2 | 1.05 |
| $A^9$-THF-γ2 | 0.86 |
| $Y^{-2}$,$A^{-1}$-THF-γ2 | 1.30 |
| $Y^{-1}$,$A^9$-THF-γ2 | 1.06 |
| $A^{-2}$,$Y^{-1}$-THF-γ2 | 1.29 |
| $A^{-1}$,$A^9$-THF-γ2 | 0.93 |
| $Y^{-2}$,$A^{-1}$,$A^9$-THF-γ2 | 1.16 |
| $A^9$,$Y^{10}$-THF-γ2 | 1.13 |
| $A^{-1}$,$A^9$,$Y^{10}$-THF-γ2 | 1.18 |
| $Y^{-2}$,$A^{-1}$,$A^9$,$Y^{10}$-THF-γ2 | 1.36 |
| Deletion analogs | |
| des-$L^1$-THF-γ2 (THF-γ28) | 0.78 |
| des-$E^2$-THF-γ2 | 1.07 |
| des-$D^3$-THF-γ2 | 1.06 |
| des-$G^4$-THF-γ2 | 0.99 |
| des-$P^5$-THF-γ2 | 0.83 |
| des-$K^6$-THF-γ2 | 1.19 |
| des-$F^7$-THF-γ2 | 0.70* |
| des-$L^8$-THF-γ2 (THF-γ17) | 0.74* |
| des-$L^1$,$E^2$-THF-γ2 (THF-γ38) | 0.75 |
| des-$L^1$,$E^2$,$D^3$-THF-γ2 (THF-γ48) | 0.64 |
| P-K-F-L (THF-γ58) | 0.64 |
| des-$F^7$,$L^8$-THF-γ2 (THF-γ16) | 0.12* |
| des-$L^1$,$L^8$-THF-γ2 (THF-γ27) | 0.59* |
| des-$L^1$,$E^2$,$L^8$-THF-γ2 (THF-γ37) | 0.57* |
| G-P-K-F (THF-γ47) | 0.52* |
| Single Substitution analogs | |
| [D]$L^1$-THF-γ2 | 1.07 |
| $S^1$-THF-γ2 | 0.78 |
| $R^1$-THF-γ2 | 0.77 |
| $Y^1$-THF-γ2 | 0.94 |
| $V^1$-THF-γ2 | 0.87 |
| $I^1$-THF-γ2 | 0.96 |
| $D^1$-THF-γ2 | 0.78 |
| $G^1$-THF-γ2 | 0.78 |
| $H^1$-THF-γ2 | 0.75 |
| $C^1$-THF-γ2 | 0.85 |
| $A^2$-THF-γ2 | 1.00 |
| $S^2$-THF-γ2 | 0.93 |
| $Q^2$-THF-γ2 | 0.91 |
| $F^2$-THF-γ2 | 1.67 |
| $R^2$-THF-γ2 | 0.88 |
| $A^3$-THF-γ2 | 1.03 |
| $R^3$-THF-γ2 | 0.81 |
| $N^3$-THF-γ2 | 0.90 |
| $S^3$-THF-γ2 | 0.92 |
| $V^3$-THF-γ2 | 1.33 |
| $F^3$-THF-γ2 | 1.82 |
| $G^3$-THF-γ2 | 0.99 |
| $A^3$-THF-γ2-NH$_2$ | 0.89* |
| (Asi)$^3$-THF-γ2* | 1.19 |
| $Y^4$-THF-γ2 | 1.27 |
| $V^4$-THF-γ2 | 1.39 |
| $D^4$-THF-γ2 | 0.83 |
| $H^4$-THF-γ2 | 0.86 |
| $S^4$-THF-γ2 | 0.94 |
| $N^4$-THF-γ2 | 0.74 |
| $K^4$-THF-γ2 | 0.69 |
| $A^4$-THF-γ2 | 1.07 |
| $A^5$-THF-γ2 | 0.85 |
| $K^5$-THF-γ2 | 0.48 |

TABLE 1-continued

Peptide Analogs of THF-γ2

| Peptide | Relative retention time[a] $R_t$ (peptide)/$R_t$ (THF-γ2)[b] |
|---|---|
| Q⁵-THF-γ2 | 0.65 |
| S⁵-THF-γ2 | 0.66 |
| E⁵-THF-γ2 | 0.76 |
| R⁵-THF-γ2 | 0.61 |
| D⁶-THF-γ2 | 1.20 |
| Y⁶-THF-γ2 | 1.63 |
| A⁶-THF-γ2 | 1.25 |
| N⁶-THF-γ2 | 1.10 |
| T⁶-THF-γ2 | 1.17 |
| I⁶-THF-γ2 | 1.75 |
| V⁷-THF-γ2 | 0.74* |
| H⁷-THF-γ2 | 0.54* |
| A⁷-THF-γ2 | 0.61* |
| S⁷-THF-γ2 | 0.60* |
| Y⁷-THF-γ2 | 0.80* |
| N⁷-THF-γ2 | 0.56* |
| E⁷-THF-γ2 | 0.61* |
| Q⁸-THF-γ2 | 0.56* |
| H⁸-THF-γ2 | 0.53* |
| K⁸-THF-γ2 | 0.53* |
| A⁸-THF-γ2 | 0.65* |
| D⁸-THF-γ2 | 0.62* |
| T⁸-THF-γ2 | 0.62* |
| Multi Substitution analogs | |
| R²,V⁴-THF-γ2 | 1.23 |
| K³,E⁴-THF-γ2 | 0.82 |
| K⁵,D⁸-THF-γ2 | 0.43* |
| T⁵,D⁸-THF-γ2 | 0.49* |
| N³,Q⁵,D⁸-THF-γ2 | 0.38* |
| N⁴,G⁶,L⁷-THF-γ2 | 0.74 |
| M¹,S⁴,V⁸-THF-γ2 | 0.76* |
| T¹,A³,E⁴,I⁸-THF-γ2 | 0.65 |
| [D]¹,³,⁵,⁷-THF-γ2 | 1.45 |
| retro-THF-γ2 (THF-γ81) | 0.88 |
| Cyclic analogs | |
| C³-C⁶-cyclic THF-γ2 L-E-C̄-G-P-C̄-F-L (SEQ ID NO: 27) | 1.63 |
| A³,C²-C⁶-cyclic THF-γ2 L-C̄-A-G-P-C̄-F-L (SEQ ID NO: 28) | 1.57 |

[a]Conditions for HPLC were: Lichrosphere 100 RP-18 (4 × 125 mm + 4 × 4 mm) 5 μm column (Merck), and a linear gradient of acetonitrile (20–50% in 30 min) in 0.1% aqueous trifluoroacetic acid, 1 ml/min; retention time of the peptide was determined by following the absorption at 214 nm.
[b]$R_t$, retention time was determined as net value by subtracting the injection delay from the measured retention times of the peptides.
[c]The single letter code for amino acids is used.
*chromatography conditions as above except for the gradient: 10–30% acetonitrile in 20 min.
‡AC = Aminocaproyl.
Asi = α Amino succinimidyl.

TABLE 2

Other Cyclic Peptide Analogs of THF-γ2

| Peptide | Relative retention time $R_t$ (peptide)/$R_t$ (THF-γ2) |
|---|---|
| 2,6-cyclic-THF-γ2 L-E-D-G-P-K-F-L | 1.18 |
| 2,6-cyclic,A³-THF-γ2 L-E-A-G-P-K-F-L | 1.26 |
| 3,6-cyclic-THF-γ2 L-E-D-G-P-K-F-L | 1.34 |

TABLE 3

Biological Activity of Peptide Analogs of THF-γ2

| Peptide | Biological activity | |
|---|---|---|
| | IL-2[1] | GM-CFC[2] |
| THF-γ2, L-E-D-G-P-K-F-L | +++ | +++ |
| Addition analogs | | |
| (THF-γ)-A-Y-A-(THF-γ2) | +++ | +++ |
| I⁹-THF-γ2 | ++ | +++ |
| Y⁻¹-THF-γ2 | ++ | ++ |
| Y⁻¹,I⁹-THF-γ2 | ++ | ++ |
| A⁻¹,A⁹-THF-γ2 | n.d. | + |
| Y⁻²,A⁻¹,A⁹-THF-γ2 | n.d. | + |
| Y⁻²,A⁻¹-THF-γ2 | n.d. | ++ |
| iodo-Y⁻¹-THF-γ2 | ++ | – |
| [D]A⁻¹-THF-γ2 | ++ | ++ |
| K⁻¹(ε-AC-biotinyl)-THF-γ2‡ | – | + |
| K⁹(ε-AC-biotinyl),[D]L⁸-THF-γ2 | n.d. | ++ |
| Deletion analogs | | |
| des-L¹-THF-γ2 (THF-γ28) | ++ | ++ |
| des-L¹,E²-THF-γ2 (THF-γ38) | + | – |
| des-E²-THF-γ2 | n.d. | + |
| Substitution analogs | | |
| R¹-THF-γ2 | n.d. | + |
| S²-THF-γ2 | ++ | ++ |
| Q²-THF-γ2 | + | – |
| A³-THF-γ2 | +++ | +++ |
| R³-THF-γ2 | ++ | ++ |
| F³-THF-γ2 | + | – |
| A³-THF-γ-NH₂ | + | – |
| Y⁴-THF-γ2 | + | + |
| V⁴-THF-γ2 | + | + |
| D⁴-THF-γ2 | ++ | – |
| S⁴-THF-γ2 | + | – |
| A⁵-THF-γ2 | + | – |
| K⁵-THF-γ2 | + | – |
| Q⁵-THF-γ2 | ++ | – |
| S⁵-THF-γ2 | +++ | – |
| R⁵-THF-γ2 | ++ | + |
| D⁶-THF-γ2 | + | – |
| Y⁶-THF-γ2 | + | – |
| N⁶-THF-γ2 | + | – |
| I⁶-THF-γ2 | – | + |
| V⁷-THF-γ2 | ++ | + |
| H⁷-THF-γ2 | + | ++ |
| A⁷-THF-γ2 | + | + |
| S⁷-THF-γ2 | ++ | – |
| Y⁷-THF-γ2 | + | – |
| N⁷-THF-γ2 | – | + |
| E⁷-THF-γ2 | – | + |
| Q⁸-THF-γ2 | + | – |
| H⁸-THF-γ2 | – | + |
| K⁸-THF-γ2 | + | – |
| K³,E⁴-THF-γ2 | – | + |
| K⁵,D⁸-THF-γ2 | – | + |
| M¹,S⁴,V⁸-THF-γ2 | ++ | – |
| N³,Q⁵,D⁸-THF-γ2 | ++ | – |
| T¹,A³,E⁴,I⁸-THF-γ2 | + | – |

[1]Enhancement of ConA induced IL-2 production in mouse spleen cells as described in Example 1, section 1.1, above.
[2]Enhancement of the number of GM-CFC from mouse bone marrow as described in Example 1, section 1.2, above.
‡AC = Aminocaproyl.

REFERENCES

1. Barak Y, Hahn T, Pecht M, Karov Y, Berrebi A, Zaizov R, Sterk B, Buchner V, Burstein Y and Trainin N. Thymic humoral factor-γ2, an immunoregulatory peptide, enhances human hematopoietic progenitor cell growth. Exp. Hematol. 20:173–177, 1992.
2. Ben-Hur H, Pecht M, Netzer L, Borenstein R, Blickman I, Burstein Y and Trainin N. Immune modulation exerted by thymic humoral factor THF-γ2 on T cell subsets and IL-2 production of umbilical cord blood lymphocytes. Immunopharmac and Immunotoxico. 12:123–133, 1990.
3. Burstein Y, Buchner V, Pecht M and Trainin N. THF-γ2: purification and amino acid sequence of an immunoregulatory peptide from calf thymus. Biochemistry 27:4066–4071, 1988.
4. Goso C, Frasca D, and Doria G. Effect of synthetic thymic humoral factor (THF-γ2) on T cell activation in immunodeficient aging mice. Clin. Exp. Immunol. 87:346–351, 1992.
5. Handzel Z. T., Burstein Y, Buchner V, Pecht M and Trainin N. Immunomodulation of T cell deficiency in humans by thymic humoral factor: from curde extract to synthetic THF-γ2. J. Biol. Res. Mod. 9:269–278, 1990.
6. Katorza E, Pacht M, Apte R. N., Benharroch D, Burstein Y, Trainin N and Rager-Zisman B. Restoration of immunological responses by THF, a thymic hormone, in mice infected with murine cytomegalovirus (MCMV). Clin. Exp. Immunol. 70:268–275, 1987.
7. Ophir R, Pecht M, Halperin D, Rashid G, Burstein Y, Ben-Efraim S and Trainin N. THF-γ2, a thymic hormone, increases immunocompetence and survival in 5-fluorouracil treated mice bearing MOPC-315 plasmacytoma. Cancer Immunol and Immunother 30:119–125, 1989.
8. Ophir R, Pecht M, Rashid G, Halperin D, Lourie S, Burstein Y, Ben-Efraim S and Trainin N. A synthetic thymic hormone, THF-γ2, repairs immunodeficiency of mice cured from plasmacytoma by Melphalan. Int. J. Cancer 45:1190–1194, 1990.
9. Ophir R, Pecht M, Relyveld E. H., Burstein Y, Ben-Efraim S, and Trainin N. THF-γ2, a synthetic thymic hormone, increases effectiveness of combined chemotherapy and immunotherapy against RPC-5 murine plasmacytoma. Int. J. Immunopharmac. 12:752–754, 1990.
10. Ophir R, Pecht M, Burstein Y, Harshemesh H, Ben-Efraim S, and Trainin N. Therapeutic effectiveness against MOPC-315 plasmacytoma of low or high doses of the synthetic thymic hormone THF-γ2 in combination with an "immunomodulating" or a "non-immunomodulating" drug. Int. J. Cancer 48: 96–100, 1991.
11. Pecht M, Lourie S, Burstein Y and Trainin N. The thymic hormone THF-γ2 selectively enhances secretion of IL-2 but not IL-6 by spleen and bone marrow cells. 8th International Congress of Immunology. Abst. Budapest, 1992.
12. Pecht M, Lourie S, Burstein Y, Zipori D. and Trainin N. Potentiation of myeloid colony formation in bone marrow of intact and neonatally thymectomized mice by the thymic hormone THF-γ2. Exp. Hematol. 21: 277–282, 1993.
13. Rager-Zisman B, Zuckerman F, Benharroch D, Pecht M, Burstein Y and Trainin N. Therapy of a fatal MCMV infection with THF-γ2 treated immune spleen cells. Clin. Exp. Immunol. 79:246–252, 1990.
14. Trainin N, Handzel Z. T. and Pecht M. Biological and clinical properties of THF. Thymus 6:137–150, 1985.
15. Trainin N, Burstein Y, Ben-Efraim S, Goebel F. D. and Handzel Z. T. The use of THF, a thymic hormone, for immunomodulation in cancer and aids. In: Novel Approaches in Cancer Therapy. Lapis & Eckhardt (eds), Karger (Basel)/Akademiai Kiado (Budapest), Vol 5, 253–260, 1987.

---

We claim:

1. A peptide being a thymic humoral factor γ2 (THF-γ2) analog of at least six amino acids or a functional derivative or a salt thereof, able to enhance by at least 30% either concanavalin A (ConA)-induced IL-2 production in mouse spleen cells and/or the number of granulocyte-monocyte colony forming cells of mouse bone marrow, said peptide having the sequence of THF-γ2 of the formula I (SEQ ID No:1):

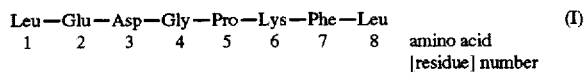

but differing therefrom by (i) deletion of one or two amino acids except for a two amino acid deletion consisting of residues 7 and 8; or (v) linkage of two to four sequences of sequence (I) or modified sequences of (I) corresponding to (i) through a peptidic or non-peptidic linkage.

2. A peptide according to claim 1 selected from a peptide of the formula:

Glu-Asp-Gly-Pro-Lys-Phe-Leu (SEQ ID No:2), or

Asp-Gly-Pro-Lys-Phe-Leu (SEQ ID No:3).

3. A pharmaceutical composition comprising a peptide as claimed in claim 1, a functional derivative or a salt thereof, and a pharmaceutically acceptable carrier.

4. A pharmaceutical composition according to claim 3 for parenteral administration.

5. A pharmaceutical composition according to claim 3 for intranasal administration.

* * * * *